US00PP21165P2

(12) United States Plant Patent
Blom

(10) Patent No.: US PP21,165 P2
(45) Date of Patent: Jul. 13, 2010

(54) ***CHRYSANTHEMUM* PLANT NAMED 'ZANMUROWA'**

(50) Latin Name: *Chrysanthemum×morifolium*
Varietal Denomination: Zanmurowa

(75) Inventor: Wilhelmus Bernardus Blom, Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 0 days.

(21) Appl. No.: 12/314,957

(22) Filed: Dec. 19, 2008

(51) Int. Cl.
*A01H 5/00* (2006.01)

(52) U.S. Cl. ..... Plt./293

(58) Field of Classification Search ..... Plt./293, Plt./287

See application file for complete search history.

*Primary Examiner*—Kent L Bell
(74) *Attorney, Agent, or Firm*—Steptoe & Johnson LLP

(57) ABSTRACT

A *chrysanthemum* plant named 'Zanmurowa' directed by its medium sized blooms with dark red ray florets and prolific branching; natural season flower date September 22–27; blooming for a period of 4–5 weeks.

3 Drawing Sheets

BACKGROUND OF THE INVENTION

The present invention relates to a new and distinct cultivar of *chrysanthemum* plant, botanically known as *Chrysanthemum×morifolium* Ramat., and hereinafter referred to by the cultivar denomination 'Zanmurowa'.

'Zanmurowa' is a product of a breeding and selection program for outdoor pot mums (garden mums) which had the objective of creating new *chrysanthemum* cultivars with a double type inflorescence, a natural season flower date starting at September 22–27; blooming for a period of 4–5 weeks. The new plant of the present invention comprises a new and distinct cultivar of *chrysanthemum* plant (to be deleted). 'Zanmurowa' is a seedling resulting from the crossing of the female parent id 70 and the male parent id 537. Plants of 'Zanmurowa' differ from plants of the female parent in growth habit, that of the seedling is more vigorous. Plants of 'Zanmurowa' differ from plants of the male parent in inflorescence size, that of the seedling is larger.

The new and distinct cultivar was discovered and selected as a flowering plant by Wilhelmus Bernardus Blom on a cultivated field in Rijsenhout, The Netherlands in 2005. The first act of asexual production of 'Zanmurowa' was accomplished when vegetative cuttings were used from the initial selection in 2005 and propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
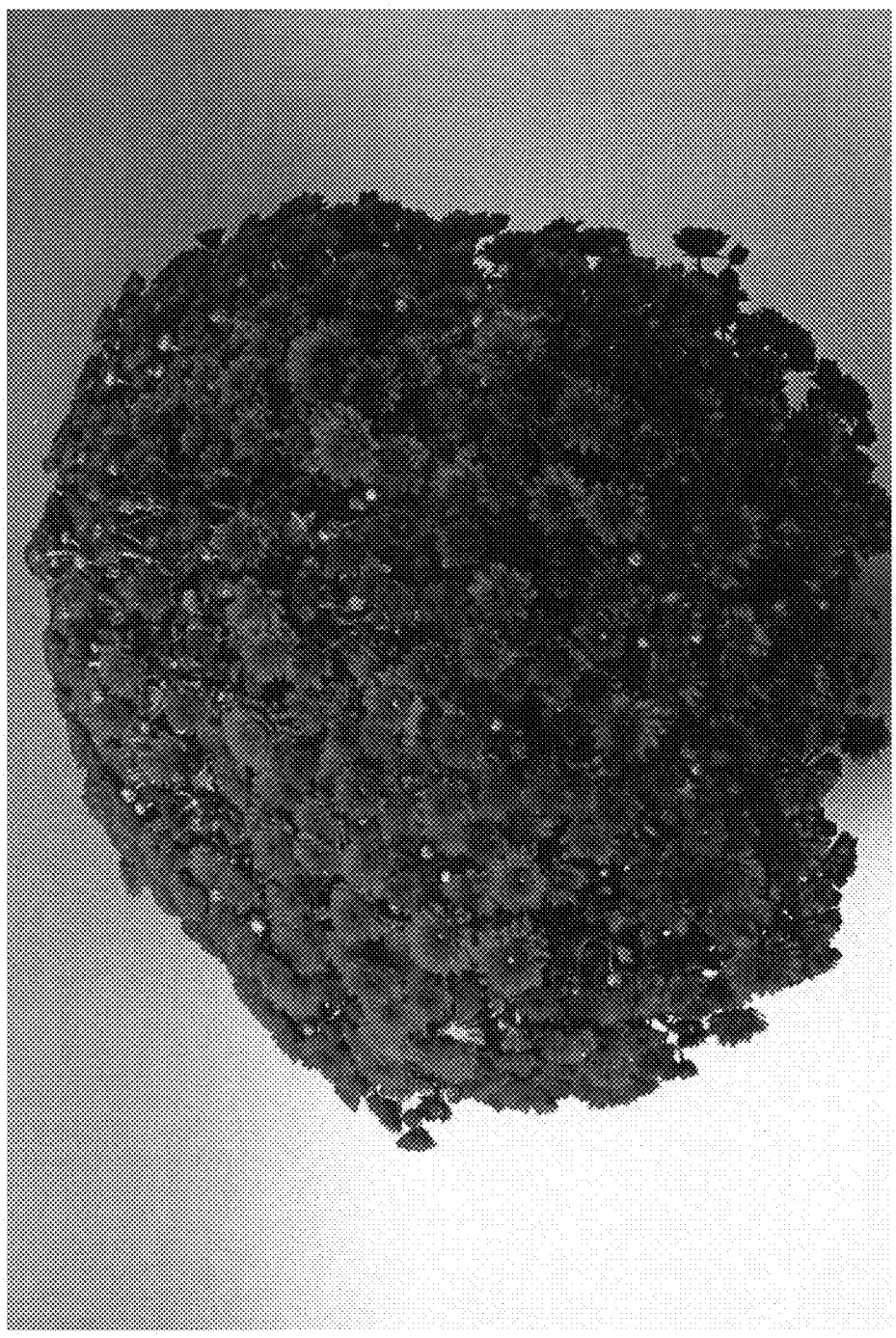
FIG. 1 shows a plant of the cultivar in full bloom.
Figure 2:
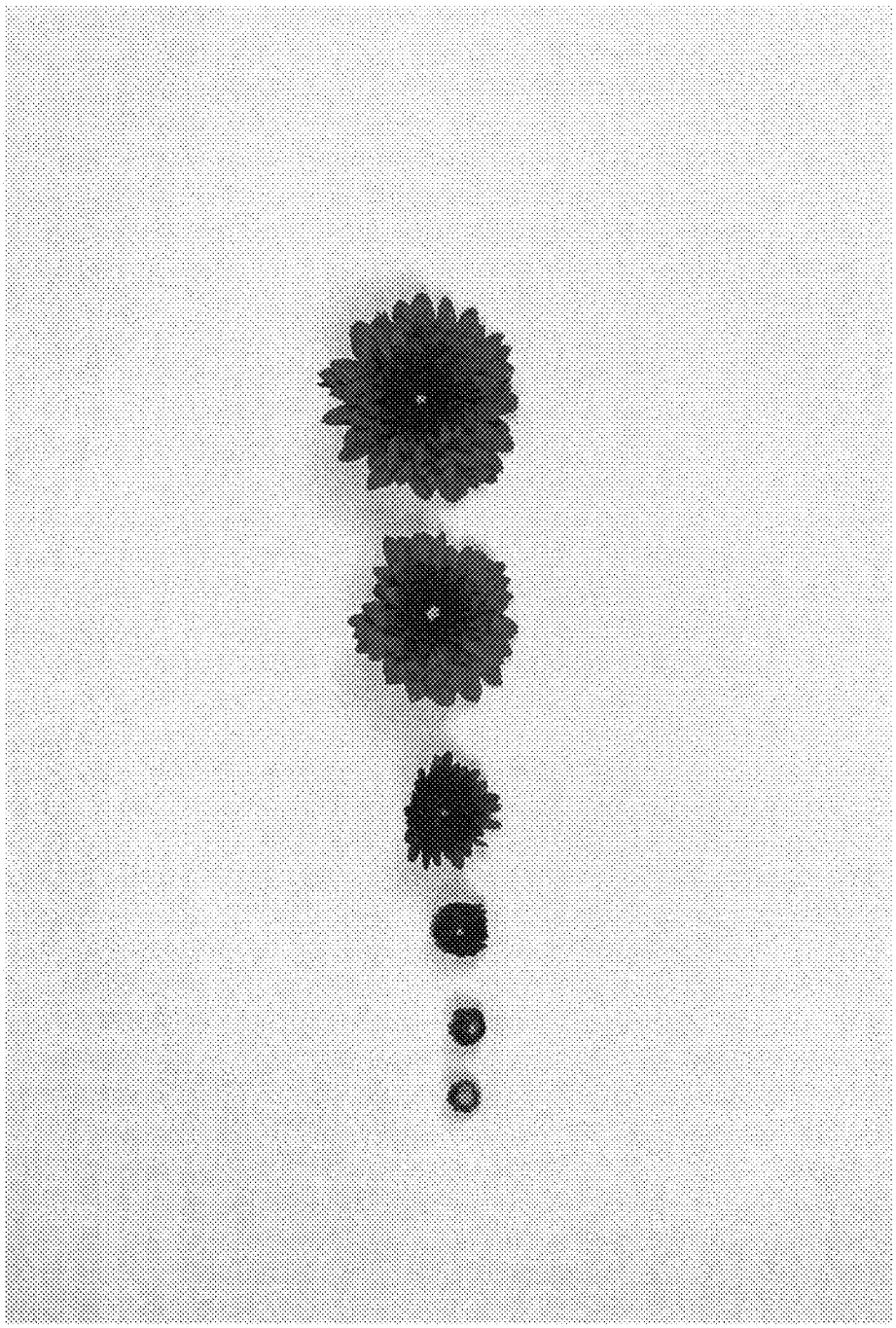
FIG. 2 shows the various stages of bloom of the new cultivar.
Figure 3:
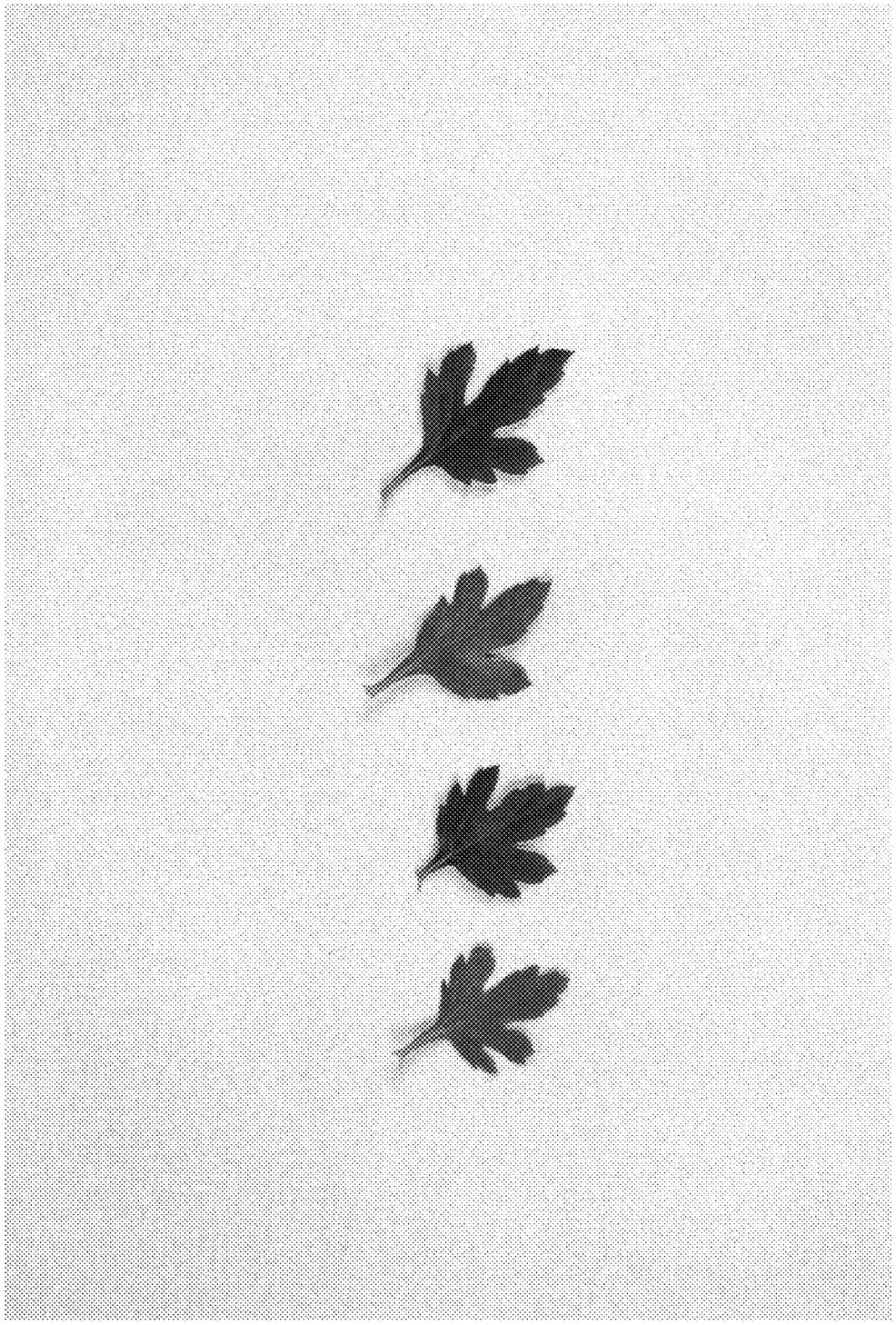
FIG. 3 shows the various stages of foliage of the new cultivar.

The observations and measurements were gathered from plants grown out door in Rijsenhout, The Netherlands under natural day length and temperature and planted in week 22 in 2008. The natural blooming date of this crop was September 22–27 (week 39) . The average height of the plants was 30 cm. No growth retardants were used. No tests were done on disease or insect resistance or susceptibility. No tests were done on cold or drought tolerance. This new variety produces medium sized blooms with dark red ray florets blooming for a period of 4–5 weeks. From the cultivars known to inventor the most similar existing cultivar in comparison to 'Zanmurowa' is 'Manakin' (U.S. Plant Pat. No. 11,521). When 'Manakin' and 'Zanmurowa' are being compared the following difference is noticed: The difference of 'Manakin' and 'Zanmurowa' are (1) Natural season blooming date. And (2) Size of bloom. (1). The natural season blooming date of 'Manakin' is mid-September, while that of 'Zanmurowa' is late September. (2). The size of the blooms of 'Manakin' is smaller than those of 'Zanmurowa'.

The following is a description of the plant and characteristics that distinguish 'Zanmurowa' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum xmorifolium* Ramat 'Zanmurowa'

| Bud | |
|---|---|
| Size | Small; cross-section 0.6 cm, height 0.4 cm |
| Shape | Oblate |
| Texture | Pubescent |

TABLE 1-continued

| Botanical Description of *Chrysanthemum xmorifolium* Ramat 'Zanmurowa' | |
|---|---|
| Outside Color | Greyed-green 191A |
| Phyllaries | |
| Number | 22-24, arranged in 3 rows |
| Shape | Elliptic |
| Apex | Acute |
| Base | Truncate |
| Margin | Entire |
| Color | Upper side: Greyed-green 191A<br>Lower side Greyed-green 191C |
| Length and width | 5 mm; 2-3 mm |
| Texture | Pubescent |
| Inflorescence | |
| Type | Double |
| Height | 2 cm |
| Diameter | 5 cm |
| Peduncle length | 9-12 cm |
| Peduncle color | Greyed-green 191 C |
| Peduncle diameter | 2 cm |
| Peduncle surface | Pubescent |
| Number per branch | Approx. 6 inflorescences |
| Flowering period individual inflorescence | 4-5 weeks |
| Seeds | Produced in small quantities, ovate, Greyed-brown 199A, length 1.5 mm diameter 0.8 mm |
| Fragrance | Faint *chrysanthemum* odor |
| Color | |
| Center of inflorescences (disc florets) | Immature stage: Yellow 9A<br>Mature stage: Yellow 12A (pollen) |
| Color of upper surface of the ray-florets | Greyed-purple 185A |
| Color of the lower surface of the ray-florets | Greyed-red 181B |
| Tonality from Distance | A garden mum with dark red inflorescences and small yellow disc |
| Color of the ray-florets after aging of the plant | Greyed-red 181A |
| Ray florets | |
| Texture | Upper and lower side smooth |
| Number | 130-140 |
| Shape | Elliptic |
| Apex | Mucronulate |
| Base | Attenuate |
| Cross-section | Flat |
| Longitudinal axis of majority | Straight |
| Length of corolla tube | 0.3-0.4 cm |
| Ray-floret margin | Entire |
| Ray-floret length | 1.6-2.7 cm |
| Ray-floret width | 2-5 cm |
| Ratio length/width | Medium |
| Disc florets | |
| Disc diameter | 2-3 mm |
| Distribution of disc florets | Moderate |
| Shape | Tubular |
| Color | Yellow 9A at apex, and Yellow 11D at base |
| Number | 8-10 |
| Length | 0.5 mm |
| Diameter | 0.3 mm |
| Receptacle | |
| Shape | Conical raised |
| Color | Green 138C |
| Height | 0.5 cm |
| Diameter | 0.6 mm |
| Reproductive Organs | |

TABLE 1-continued

| Botanical Description of *Chrysanthemum xmorifolium* Ramat 'Zanmurowa' | |
|---|---|
| Androecium | Present in disc florets only |
| Stamen length | 3 mm |
| Stamen color | Yellow-green 144A |
| Anther color | Yellow 3A |
| Pollen | Moderate |
| Pollen | Yellow 12A |
| Gynoecium | Present in both ray and disc florets |
| Style color | Yellow-green 154C |
| Style Length | 3 mm |
| Stigma color | Yellow 7A |
| Stigma Width | 1 mm |
| Ovary | Enclosed in calyx |
| Plant | |
| Form | Grown as a potmum, outdoor raised and mounded |
| Growth habit | Spherical shape |
| Growth rate | Medium |
| Height | 30 cm |
| Width | 40 cm |
| Stem Color | Greyed-brown 199A |
| Stem Strength | Strong |
| Stem Brittleness | Not brittle |
| Stem Anthocyanin Coloration | Not observed |
| Internode length | 1-2 cm |
| Length of lateral branch | From top to bottom 20 cm |
| Lateral branch color | Green 137C |
| Lateral branch diameter | 2 mm |
| Lateral branch brittleness | Medium |
| Branching (average number of lateral branches) | Prolific with 8 breaks after pinching |
| Natural season blooming date | September 22-27 to late October |
| Foliage | |
| Leaf color | Upper side: Green 137A<br>Lower side: Green 138A |
| Color midvein | Upper side: Yellow-green 147D<br>Lower side: Yellow-green 148D |
| Size | Small.; length 3.5-5 cm, width 2-2.5 cm |
| Quantity (number per lateral branch) | 22 -24 |
| Shape | Elliptic |
| Texture upper side | Sparsely pubescent |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Attenuate |
| Apex | Mucronulate |
| Petiole length | 0.5-1 cm |
| Petiole diameter | 2 mm |
| Petiole color | Yellow-green 147D |

TABLE 2

| Differences with the comparison variety | | |
|---|---|---|
| | 'Zanmurowa' | 'Manakin' |
| Natural season blooming date | Late September | Mid-September |
| Bloom diameter | 5 cm | 3.5 cm |

I claim:

1. A new and distinct variety of *chrysanthemum* plant as described and illustrated.

* * * * *